United States Patent [19]
Nakat

[11] Patent Number: 5,401,494
[45] Date of Patent: Mar. 28, 1995

[54] COMPOSITIONS

[75] Inventor: Sarangdhar S. Nakat, Cidco, India

[73] Assignee: Sandoz Ltd., Basel, Switzerland

[21] Appl. No.: 10,226

[22] Filed: Jan. 27, 1993

[30]   Foreign Application Priority Data

Jan. 31, 1992 [GB]  United Kingdom ............... 9202060

[51] Int. Cl.$^6$ .................. A61K 31/215; A61K 49/00; A01N 37/34; A01N 53/00
[52] U.S. Cl. .................................... 424/10; 514/461; 514/521; 514/531; 514/533; 514/538
[58] Field of Search ............... 424/10; 514/461, 521, 514/531, 533, 538

[56]    References Cited
     U.S. PATENT DOCUMENTS 4,617,318  10/1986  Marei .................................. 514/520

FOREIGN PATENT DOCUMENTS

| | | |
|---|---|---|
| 0001454 | 4/1979 | European Pat. Off. . |
| 60-237006 | 11/1985 | Japan . |
| 1197402 | 8/1989 | Japan . |
| 1305013 | 12/1989 | Japan . |
| 2108604 | 4/1990 | Japan . |
| 3251538 | 11/1991 | Japan . |
| 3291221 | 12/1991 | Japan . |
| 9008467 | 8/1990 | WIPO . |

OTHER PUBLICATIONS

K. Naumann, pp. 116 to 141 in Chemistry of Plant Protection, Springer Berlin, 1990.
Awasthi, C. A., vol. 106, (1987), 106:14,685w.

*Primary Examiner*—Allen J. Robinson
*Attorney, Agent, or Firm*—Allen E. Norris

[57]    ABSTRACT

Agricultural compositions comprising paraesthetic agrochemicals, such as pyrethroids, and an amount of urea effective to reduce the paraesthetic effect of such agrochemicals.

3 Claims, No Drawings

COMPOSITIONS

This application is directed to an agricultural composition having an improved sensory effect. More particularly, this application is directed to an agricultural composition demonstrating a reduced level of paraesthesia.

Certain agricultural compounds can, under various conditions, be paraesthetic to particularly sensitive subjects. This effect is manifested normally by a burning or prickling sensation on the skin. It has now been found that the level of paraestheticity of agrochemicals in particular pesticides including insecticides and acaricides can be appreciably reduced by employing such agrochemicals in conjunction with and amount of urea capable of reducing the paraesthetic effect of the employed agrochemical.

This application particularly concerns insecticidal or acaricidal pesticides loosely referred to as "pyrethroids" in the art which can be paraesthetic. Representative pyrethroids, all of which are known, are allethrin, prallethrin, furethrin, acrinathrin, bifenthrin, cyfluthrin, cyhalothrin, cypermethrin, deltamethrin, cyphenothrin, permethrin, phenothrin, resmethrin, tefluthrin, tetramethrin, dimethrin, fenfluthrin, pyresmethrin, terallethrin, tralomethrin, tralocytrin, flumethrin, cycloprothrin, fenvalerate, fluvalinate, pyriproxyfen, etofenprox, fenpropathrin, lambda-cyhalothrin, esfenvalerate, alpha-cypermethrin, beta-cyfluthrin.

Pyrethroids are very active broad spectrum insecticides. Pyrethroids (including pyrethrins) can be grouped together based on their similar overall shape, physical properties (especially polarity) and mode of action at nerve membranes. The changes in nerve membrane ionic permeability are mediated by discrete molecular structures, called ionic channels, which are formed by proteins embedded in the lipid matrix of the membrane. The control of sodium ion permeability through the nerve membrane is vital to nerve function and the resting membrane is electrically polarized. Pyrethroids act stereoselectively on a small fraction of the fast voltage-dependent sodium ion channels in excitable nerve membranes in several parts of the insect nervous system. The major initial effect is to delay the closing of the sodium ion channel activation gate. The prolongation of the transient inward sodium ion movement through the nerve membrane produces membrane depolarization which causes eventually a block of nerve impulses and results in the intoxication symptoms typical for pyrethroids.

Particular pyrethroids of interest in this application are of the formula (I)

$$X-C(O)-O-CHR_1-Y \quad (I)$$

wherein
X is

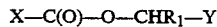

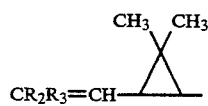

or

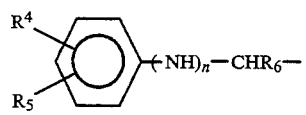

Y is 3-phenoxyphenyl wherein the phenyl is optionally halogen substituted; or 5-benzyl-3-furyl;

$R_1$ is hydrogen or cyano;

$R_2$ and $R_3$ are independently selected from halogen; $C_{1-4}$alkyl optionally substituted by halogen; phenyl optionally substituted by halogen; and $C_{2-5}$alkoxycarbonyl;

$R_4$ and $R_5$ are independently selected from hydrogen; halogen; and $C_{1-4}$alkyl optionally substituted by halogen;

$R_6$ is $C_{1-4}$alkyl; and n is 0 or 1.

Alkyl as used herein includes both branched and unbranched carbon chains.

Halogen as used herein includes chloro, bromo and fluoro.

$R_1$ is preferably cyano.

$R_2$ and $R_3$ are preferably selected from halogen, methyl, trifluoromethyl and phenyl substituted by chloro.

$R_4$ and $R_5$ are preferably selected from hydrogen, chloro and trifluoromethyl.

$R_6$ is preferably isopropyl.

Particular compounds or interest of the formula (I) are fluvalinate, fenvalerate and cypermethrin.

Compounds of the formula (I) and procedures for their syntheses are either known or in cases of novel compounds, can be produced according to procedures which are analogous to know procedures.

Compositions containing the active ingredient and urea can be formulated in the same manner as is known for formulating the active ingredient per se. They may be employed in either solid or liquid forms, e.g. in the form of a wettable powder or an emulsifiable concentrate incorporating conventional diluents. Such compositions may be produced in a conventional manner, e.g. by mixing the active ingredient with a diluent and optionally other formulating ingredients such as surfactants.

The term diluents as used herein means any liquid or solid agriculturally acceptable material which may be added to the active constituent to bring it in an easier or improved applicable form, respectively to a usable or desirable strength of activity. It can for example be talc, kaolin, diatomaceous earth, xylene or water.

Particular formulations to be applied in spraying forms such as water dispersible concentrates or wettable powders may contain surfactants such as wetting and dispersing agents, e.g. the condensation product of formaldehyde with napththalene sulphonates, an alkylarylsulphonate, a lignin sulphonate, a fatty alkyl sulphate, an ethoxylated alkylphenol and an ethoxylated fatty alcohol.

In general the formulations include from 0.01 to 90% by weight of the combination of active agent and urea, from 0 to 20% by weight of agriculturally acceptable surfactant and 99.99 to 10% by weight (solid or liquid) diluent(s).

The proportion of urea to active ingredient will vary according to use, particular type of active ingredient, etc. but will typically range in parts by weight urea:active ingredient from 0.001:1 to 4:1, e.g. from 0.001:1 to 2:1. Particularly good results are obtained when the weight by weight proportion of urea to active ingredient is in the range of from 1:25 to 4:1, more particularly in the range of from 2:1 to 4:1.

The compositions of this application can be employed to combat insects and/or acari using application techniques and dosage rates that are known for the active ingredient.

EXAMPLE

Assessment of influence of urea on pyrethroid mediated skin sensory stimulation effects on guinea pig flank model Test product MAVRIK Aquaflow containing 22.6% by weight of taufluvalinate is applied at concentrations of 10%, 5%, 2.5% and 1% by weight a.i., respectively, by dilution in water, without or with the addition of 10%, 5%, 2.5% and 1% by weight of urea, in a volume of 0.1 ml.

Dosage per animal 0.1 ml of the test product is spread over a clipped area of approx. 30 mm×30 mm of the right flank of the animal. 0.1 ml of water serves as the vehicle control applied to a clipped area of 30 mm×30 mm at the left flank. Clipping of the fur is done approx. 24 hrs. before the application of the test product. The skin is inspected immediately before application for signs and reactions to clipping.

Pilot study

The maximal dose-response for each concentration and the time course for reaching the peak in the evoqued sensory effect is determined in a pilot study using two animals per selected dose level (10%, 5%, 2.5% and 1%) of MAVRIK Aquaflow. The effect of urea versus water is evaluated using two animals.

After a waiting period of at least one week after the dose application, each experiment is repeated in the same animal using now the test site as the control site and vice versa. So, each concentration of MAVRIK Aquaflow is tested twice per animal.

Main Study

The concentration of MAVRIK Aquaflow which gives the optimal dose-response in the pilot study is used in the main study. Four concentrations of urea are evaluated: 10%, 5%, 2.5% and 1%. Four animals are assigned for each dose evaluation of urea. The experiment is also duplicated per animal using the test site as the control site and vice versa.

Behavioural responses

Behavioural observations are made starting at 3 hrs till 15 hrs (in maximum) after each dose application. In the dark period a dim light (<100 Lux) is used. This observation period is shortened in the main study to cover a reasonable time period after the peaking in activity has been determined in the pilot study.

For each animal and each dose group the behavioural reactions are continuously recorded with an unmanned video camera using up to four (long play) or eight (normal play) videotapes.

Thus, each video tape covers an observation period up to 90 min. or 3 hrs in maximum. The monitor is placed outside the animal room. Reactions such as licking or biting the test sites are quantified by counting the number of times the animals responds (head-turns) to the pyrethroid/urea painted test site versus the untreated control site. Only full head-turns are taken into account. Mean values and S.D. are calculated from the number of reactions revealed by each concentration tested.

For reporting, a 5-min. period is considered as the standard time unit for the assessment of the behavioural reactions. One such time unit per hour of recording is regarded as sufficient to evaluate the dose-dependent behavioural reactions.

Statistical Analysis

To determine if the test product causes greater stimulation than the vehicle alone, and if the test compound alone produces a greater stimulation than the test compound to which urea was added, the response for each animal to the test flank is compared to the response to the control flank and by taking into account any modulatory effect of urea, respectively.

Based on the observations it can be concluded that urea has an inhibitory effect on the pyrethroid-induced skin sensory stimulation effect in the guinea pig flank mode.

For test concentrations of 2.5% active ingredient of MAVRIK ® Aquaflow the inhibitory effect is particularly pronounced after addition of 5% and 10% of urea.

I claim:

1. A method of reducing the paraesthetic effect of a pyrethroid demonstrating paraesthesia on a host susceptible to paraesthesia which comprises employing said pyrethroid in conjunction with an amount of urea capable of reducing the paraesthetic effect of said pyrethroid.

2. The method of claim 1, wherein the pyrethroid is of formula (I)

$$X-C(O)-O-CHR_1-Y \qquad (I)$$

wherein
X is

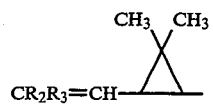

or

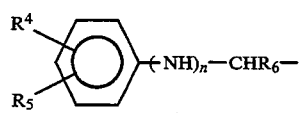

Y is 3-phenoxyphenyl wherein the phenyl is optionally halogen substituted; or 5-benzyl-3-furyl;
$R_1$ is hydrogen or cyano;
$R_2$ and $R_3$ are independently selected from halogen; $C_{1-4}$alkyl optionally substituted by halogen; phenyl optionally substituted by halogen; and $C_{2-5}$alkoxycarbonyl;
$R_4$ and $R_5$ are independently selected from hydrogen; halogen; and $C_{1-4}$alkyl optionally substituted by halogen;
$R_6$ is $C_{1-4}$alkyl; and
n is 0 or 1.

3. The method of claim 2, wherein the pyrethroid is cypermethrin, fenvalerate or fluvalinate.

* * * * *